(12) United States Patent
Kitagawa et al.

(10) Patent No.: US 11,564,570 B2
(45) Date of Patent: Jan. 31, 2023

(54) BIOLOGICAL INFORMATION MEASURING APPARATUS, METHOD AND PROGRAM

(71) Applicants: OMRON CORPORATION, Kyoto (JP); OMRON HEALTHCARE CO., LTD., Kyoto (JP)

(72) Inventors: Tsuyoshi Kitagawa, Kyoto (JP); Shingo Yamashita, Kyoto (JP); Hiroyuki Kinoshita, Kyoto (JP); Yuki Ota, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 435 days.

(21) Appl. No.: 16/554,848

(22) Filed: Aug. 29, 2019

(65) Prior Publication Data
US 2019/0380580 A1 Dec. 19, 2019

Related U.S. Application Data

(63) Continuation of application No. PCT/JP2018/009567, filed on Mar. 12, 2018.

(30) Foreign Application Priority Data

Mar. 15, 2017 (JP) .............................. JP2017-050616

(51) Int. Cl.
*A61B 5/00* (2006.01)
*A61B 5/021* (2006.01)

(52) U.S. Cl.
CPC ........ *A61B 5/0004* (2013.01); *A61B 5/02116* (2013.01); *A61B 5/721* (2013.01);
(Continued)

(58) Field of Classification Search
CPC ... A61B 5/0004; A61B 5/02116; A61B 5/721; A61B 5/681; A61B 5/6824;
(Continued)

(56) References Cited

U.S. PATENT DOCUMENTS

| 5,033,471 A | 7/1991 | Yokoe et al. |
| 2002/0138010 A1 | 9/2002 | Oka |

(Continued)

FOREIGN PATENT DOCUMENTS

| CN | 101327121 | 12/2008 |
| CN | 104138253 | 11/2014 |

(Continued)

OTHER PUBLICATIONS

International Preliminary Report on Patentability dated Sep. 19, 2019 in International (PCT) Application No. PCT/JP2018/009567.
(Continued)

*Primary Examiner* — Sean P Dougherty
*Assistant Examiner* — Alexander H Connor
(74) *Attorney, Agent, or Firm* — Wenderoth, Lind & Ponack, L.L.P.

(57) ABSTRACT

A biological information measuring apparatus includes a detector, a measuring unit, a calculator, and a determining unit. The detector detects pulse waves continuously. The measuring unit measures first biological information. The calculator calculates second biological information from the pulse waves based on the first biological information. The measuring unit suspends the measurement and resumes the measurement after a lapse of a period in a case where the determining unit does not determine that the result of measurement is normal, and the measuring unit continues the measurement in other cases where the body motion is not generated, the pulse waves are not irregular or the blood pressure value fails to vary.

11 Claims, 8 Drawing Sheets

(52) U.S. Cl.
CPC ............... *A61B 2560/0223* (2013.01); *A61B 2562/0219* (2013.01)

(58) Field of Classification Search
CPC . A61B 5/02225; A61B 5/7207; A61B 5/7221; A61B 2560/0223; A61B 2562/0219; A61B 2562/0247
See application file for complete search history.

(56) References Cited

U.S. PATENT DOCUMENTS

| | | | | |
|---|---|---|---|---|
| 2013/0226010 | A1* | 8/2013 | Hotta | A61B 5/0205 |
| | | | | 600/483 |
| 2014/0276145 | A1* | 9/2014 | Banet | A61B 5/1118 |
| | | | | 600/490 |
| 2015/0366473 | A1 | 12/2015 | Shimuta et al. | |
| 2016/0360972 | A1 | 12/2016 | Kusakabe et al. | |
| 2017/0042433 | A1 | 2/2017 | Noh et al. | |
| 2017/0095215 | A1* | 4/2017 | Watson | A61B 5/0002 |
| 2019/0209030 | A1* | 7/2019 | Shimuta | A61B 5/1116 |

FOREIGN PATENT DOCUMENTS

| | | |
|---|---|---|
| CN | 105007809 | 10/2015 |
| CN | 106419878 | 2/2017 |
| JP | 1-242031 | 9/1989 |
| JP | 11-206723 | 8/1999 |
| JP | 2002-272690 | 9/2002 |
| JP | 2004-113368 | 4/2004 |
| JP | 2005-312741 | 11/2005 |
| JP | 2008-12230 | 1/2008 |
| JP | 2012-200512 | 10/2012 |
| JP | 2015-213686 | 12/2015 |
| JP | 2017-29602 | 2/2017 |
| WO | 2008/007549 | 1/2008 |

OTHER PUBLICATIONS

Office Action dated Aug. 19, 2021 in corresponding Chinese Patent Application No. 201880017643.3, with English-language translation.

International Search Report dated Apr. 17, 2018 in International (PCT) Application No. PCT/JP2018/009567 with English translation.

* cited by examiner

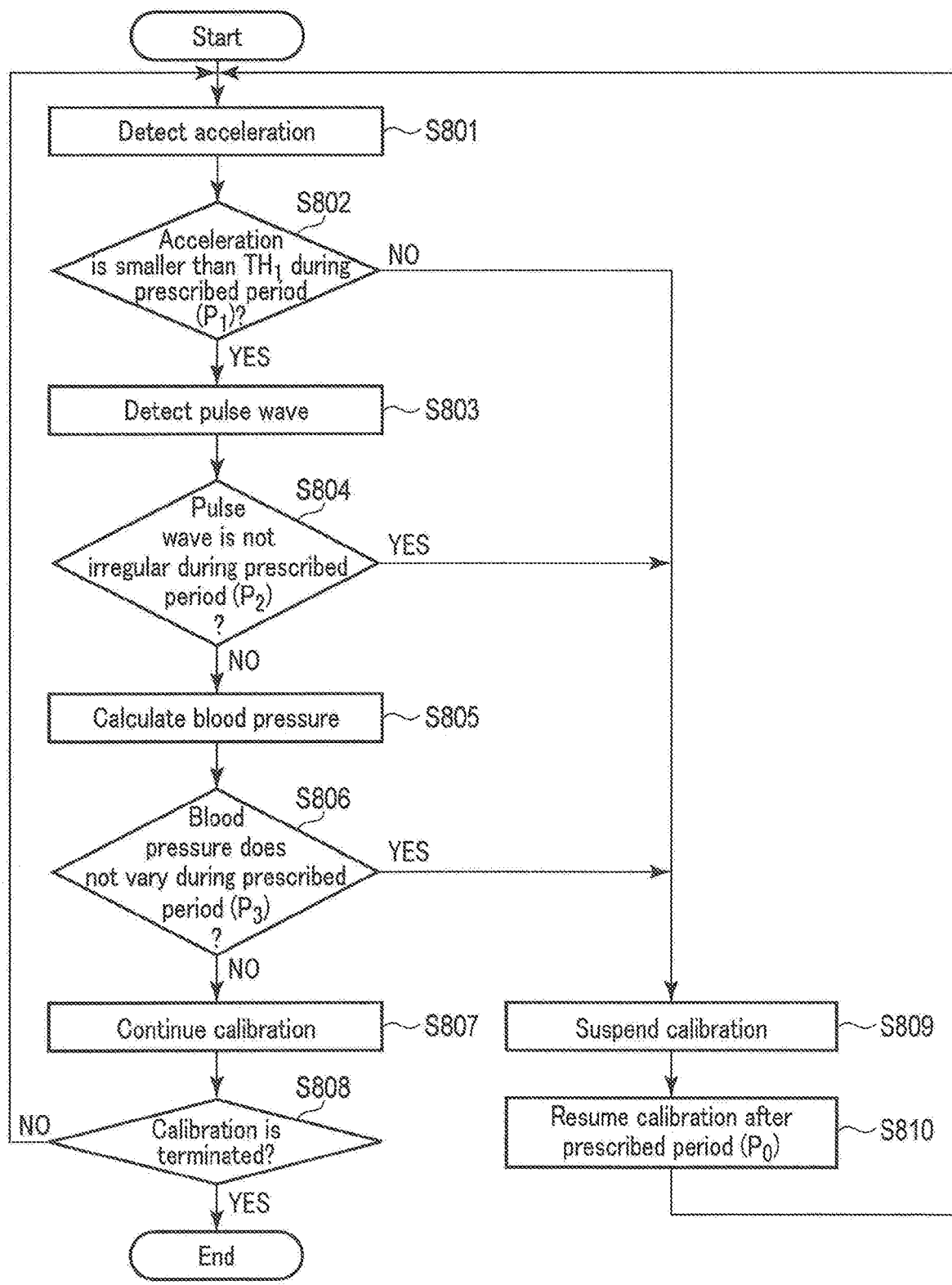
F I G. 8

BIOLOGICAL INFORMATION MEASURING APPARATUS, METHOD AND PROGRAM

CROSS-REFERENCE TO RELATED APPLICATIONS

This application is a Continuation Application of PCT Application No. PCT/JP2018/009567, filed Mar. 12, 2018 and based upon and claiming the benefit of priority from Japanese Patent Application No. 2017-050616, filed Mar. 15, 2017, the entire contents of all of which are incorporated herein by reference.

FIELD

This invention relates to a biological information measuring apparatus, a method and a program for measuring biological information continuously.

BACKGROUND

Detecting and treating a biological abnormality early using biological information has gradually been becoming important to medical care because of an environment in which a high-performance sensor can easily be used with the development of sensor technologies.

A biological information measuring apparatus is known which is capable of measuring biological information about pulse, blood pressure and the like, using information detected by a pressure sensor that is in direct contact with a biological portion through which the arteries such as the radial artery of a user's wrist pass (see, for example, Jpn. Pat. Appln. KOKAI Publication No. 2004-113368).

The blood pressure measuring apparatus described in Jpn. Pat. Appln. KOKAI Publication No. 2004-113368 calculates a blood pressure value using a cuff in a portion different from a biological portion with which a pressure sensor is brought into contact to generate calibration data from the calculated blood pressure value. Then, the pressure pulse wave detected by the pressure sensor is calibrated using the calibration data to calculate a blood pressure value for each beat.

Since however, the blood pressure measuring apparatus described in Jpn. Pat. Appln. KOKAT Publication No. 2004-113368 is large, the accuracy of measurement is difficult to increase. Since, furthermore, the blood pressure measuring apparatus is based on the premise that it is used in the limited environment and operated by a specific person, it is difficult to use for daily medical treatment and home medical care. Since, moreover, the blood pressure measuring apparatus is provided with a number of tubes and wires and is annoying, it is impractical to use the apparatus routinely and during sleep.

In addition, it is not certain that the blood pressure apparatus for calibration can make normal measurement. For example, it is likely that the pulse waves will become irregular during their calibration and influence the blood pressure.

SUMMARY

A first aspect of the invention is a biological information measuring apparatus including a detector that detects pulse waves continuously in terms of time, a measuring unit that measures first biological information intermittently, a calculator that calculates second biological information from the pulse waves based on the first biological information, and a calibrated blood pressure determining unit that determines whether a result of measurement of the measuring unit is normal. The measuring unit suspends the measurement in a case where the calibrated blood pressure determining unit does not determine that the result of measurement is normal and resumes the measurement after a lapse of a prescribed period.

A second aspect of the invention is a biological information measuring apparatus including a sensing apparatus and a calibrating apparatus. The calibrating apparatus includes a measuring unit that measures first biological information intermittently and a transmission unit that transmits data containing the first biological information to the sensing apparatus. The sensing apparatus includes a detector that detects pulse waves continuously in terms of time, a reception unit that receives the first biological information, a calculator that calculates second biological information from the pulse waves based on the first biological information, a calibrated blood pressure determining unit that determines whether a result of measurement of the measuring unit is normal. The measuring unit suspends the measurement in a case where the calibrated blood pressure determining unit does not determine that the result of measurement is normal and resumes the measurement after a lapse of a prescribed period, and the measuring unit continues the measurement in other cases.

A third aspect of the invention is the biological information measuring apparatus further including a body motion detector. The calculator calibrates the pulse waves by the first biological information and calculates second biological information from the calibrated pulse waves. The calibrated blood pressure determining unit includes a body motion determining unit that determines whether body motion is generated during a first period of the measurement of the first biological information before the pulse waves are calibrated, a pulse wave determining unit that determines whether the pulse waves are irregular during a second period of the measurement of the first biological information before the pulse waves are calibrated, and a blood pressure determining unit that determines whether a blood pressure value varies during a third period of the measurement of the first biological information before the pulse waves are calibrated. The measuring unit continues the measurement when body motion is not generated during the first period, the pulse waves are not irregular during the second period, or the blood pressure value does not vary during the third period.

A fourth aspect of the invention is the biological information measuring apparatus in which that the calculator calibrates the pulse waves by the first biological information and calculates second biological information from the calibrated pulse waves, the sensing apparatus further includes a body motion detector that detects body motion information of the calibrating apparatus, the calibrated blood pressure determining unit includes a body motion determining unit that determines whether body motion is generated during a first period of the measurement of the first biological information before the pulse waves are calibrated, based on the body motion information, a pulse wave determining unit that determines whether the pulse waves are irregular during a second period of the measurement of the first biological information before the pulse waves are calibrated, based on the pulse waves, and a blood pressure determining unit that determines whether a blood pressure value varies during a third period of the measurement of the first biological information before the pulse waves are calibrated, based on the second biological information. The measuring unit continues the measurement when at least one of determinations that body motion is not generated during the first period, the pulse waves are not irregular during the second period, and the blood pressure value does not vary during the third period, is made.

A fifth aspect of the invention is the biological information measuring apparatus in which the measuring unit suspends the measurement when it is determined that body motion is generated during the first period, it is determined that the pulse waves are irregular during the second period, or it is determined that the blood pressure value varies during the third period, and the measuring unit resumes the measurement after a lapse of a prescribed period.

A sixth aspect of the invention is the biological information measuring apparatus in which the body motion detector includes an acceleration sensor, and the body motion determining unit determines that body motion is generated when acceleration indicated by the acceleration sensor is larger than a first threshold value during the first period, the pulse wave determining unit determines that the pulse waves are irregular when a period during which an amplitude of the pulse waves is smaller than a second threshold value is longer than a prescribed period of time during the second period, and the blood pressure determining unit determines that the blood pressure value varies when increase or decrease of each of the amplitude of the pulse waves, systolic blood pressure and diastolic blood pressure for each beat exceeds a third threshold value.

A seventh aspect of the invention is the biological information measuring apparatus in which the measuring unit measures the first biological information with higher accuracy than the second biological information detected from the detector.

An eighth aspect of the invention is the biological information measuring apparatus in which the detector detects the pulse waves for each beat, and the first biological information and the second biological information are blood.

According to the first aspect of the invention, since the biological information measuring apparatus is compacted by the detector that detects pulse waves continuously in terms of time and the measuring unit that measures biological information intermittently, it can easily be attached to perform measurement and is highly convenient for the user. Since, furthermore, the measuring unit only measures the biological information intermittently, the time for the measuring unit to interfere with the user is shortened. In addition, it is determined whether a result of the measurement is normal to determine whether the measuring unit continues measuring the first biological information or suspends the measurement and resumes it after a prescribed period. The pulse waves can thus be calibrated correctly.

According to the second aspect of the invention, since the sensing apparatus includes a detector that detects pulse waves continuously in terms of time and is separated from the calibrating apparatus, it is compacted and easily placed in a position where it can reliably acquire the pulse waves. The calibrating apparatus can measure the first biological information intermittently to calculate accurate biological information from the pulse waves, and the user can easily obtain high-accuracy biological information. Since, furthermore, the measuring unit only measures the biological information intermittently, the time for the measuring unit to interfere with the user is shortened. Since, moreover, the calibrating apparatus is independent, it can be located to easily perform calibration without depending on the placement of the sensing apparatus. In addition, it is determined whether a result of the measurement of the measuring unit is normal to determine whether the measuring unit continues measuring the first biological information or suspends the measurement and resumes it after a prescribed period. The pulse waves can thus be calibrated correctly.

According to the third aspect of the invention, since the biological information measuring apparatus is compacted by the detector that detects pulse waves continuously in terms of time and the measuring unit that measures biological information intermittently, it can easily be attached to perform measurement and is highly convenient for the user. Since, furthermore, the measuring unit only measures the biological information intermittently, the time for the measuring unit to interfere with the user is shortened. In addition, it is determined whether body motion is generated during a first period of the measurement of the first biological information, whether the pulse waves are irregular during a second period of the measurement of the first biological information, and whether a blood pressure value varies during a third period of the measurement of the first biological information based on the second biological information to determine whether the measuring unit continues or suspends the measurement of the first biological information. The pulse waves can thus be calibrated correctly.

According to the fourth aspect of the invention, since the sensing apparatus includes a detector that detects pulse waves continuously in terms of time and a transmission unit that transmits data containing the pulse waves to the calibrating apparatus and is separated from the calibrating apparatus, it is compacted and easily placed in a position where it can reliably acquire the pulse waves. The calibrating apparatus measures the first biological information intermittently, receives the data from the sensing apparatus, calibrates the pulse waves by the first biological information, calculates the second biological information from the calibrated pulse waves, and calibrates the pulse waves based on the biological information measured by the measuring unit. Accurate biological information can thus be calculated from the pulse waves, and the user can easily obtain high-accuracy biological information. Since, furthermore, the measuring unit only measures the biological information intermittently, the time for the measuring unit to interfere with the user is shortened. Since, moreover, the calibrating apparatus is independent, it can be located to easily perform calibration without depending on the placement of the sensing apparatus. In addition, it is determined whether body motion is generated during a first period of the measurement of the first biological information, whether the pulse waves are irregular during a second period of the measurement of the first biological information, and whether a blood pressure value varies during a third period of the measurement of the first biological information based on the second biological information to determine whether the measuring unit continues or suspends the measurement of the first biological information. The pulse waves can thus be calibrated correctly.

According to the fifth aspect of the invention, when it is determined that body motion is generated, it is determined that the pulse waves are irregular or it is determined that the blood pressure value varies, the measuring unit can determine it as an inadequate condition for calibration to suspend the measurement and avoid calibrating the pulse waves with low accuracy. Furthermore, the measuring unit suspends the measurement and resumes it after a lapse of a prescribed period to start the calibration and repeat the suspension of the measuring unit and the calibration after a lapse of a prescribed period until an adequate calibration is completed. Correct calibration can thus be achieved.

According to the sixth aspect of the invention, it is determined that body motion is generated when acceleration indicated by the acceleration sensor is larger than a first threshold value, it is determined that the pulse waves are irregular when a period during which an amplitude of the pulse waves is smaller than a second threshold value is longer than a prescribed period of time, and it is determined that the blood pressure value varies when increase or decrease of each of the amplitude of the pulse waves, systolic blood pressure and diastolic blood pressure for each beat exceeds a third threshold value. It is thus possible to correctly determine whether to continue a calibrating operation or stop the calibrating operation and resume it after a lapse of a prescribed period. Correct calibration can thus be achieved.

According to the seventh aspect of the invention, since the first biological information is measured with higher accuracy than the second biological information detected from the detector, the accuracy of the biological information obtained based on the pulse waves from the detector can be secured and thus the biological information can be calculated with accuracy continuously in terms of time.

According to the eighth aspect of the invention, since the detector detects the pulse waves for each beat and the first biological information and the second biological information are blood, the biological information measuring apparatus can measure blood pressure for each beat continuously in terms of time.

In summary, according to each of the aspects of the invention, there can be provided a biological information measuring apparatus that can always be attached to calibrate biological information continuously in terms of time and acquire correct information, a method, and a program.

BRIEF DESCRIPTION OF THE DRAWINGS

FIG. 8 is a flowchart for determining whether to continue blood measurement for calibration of the blood pressure measuring apparatus of FIG. 1 or 7.

DETAILED DESCRIPTION

A biological information measuring apparatus, a method and a program according to an embodiment of this invention will be described below with reference to the drawings. Note that in the following embodiment, the portions denoted by the same numeral perform similar operations and their overlapping descriptions will be omitted.

The embodiments have been developed in consideration of the foregoing situation and its object is to provide a biological information measuring apparatus that can always be attached to calibrate biological information continuously in terms of time and acquire correct information, a method and a program.

(Integral Type)

Figure 1:
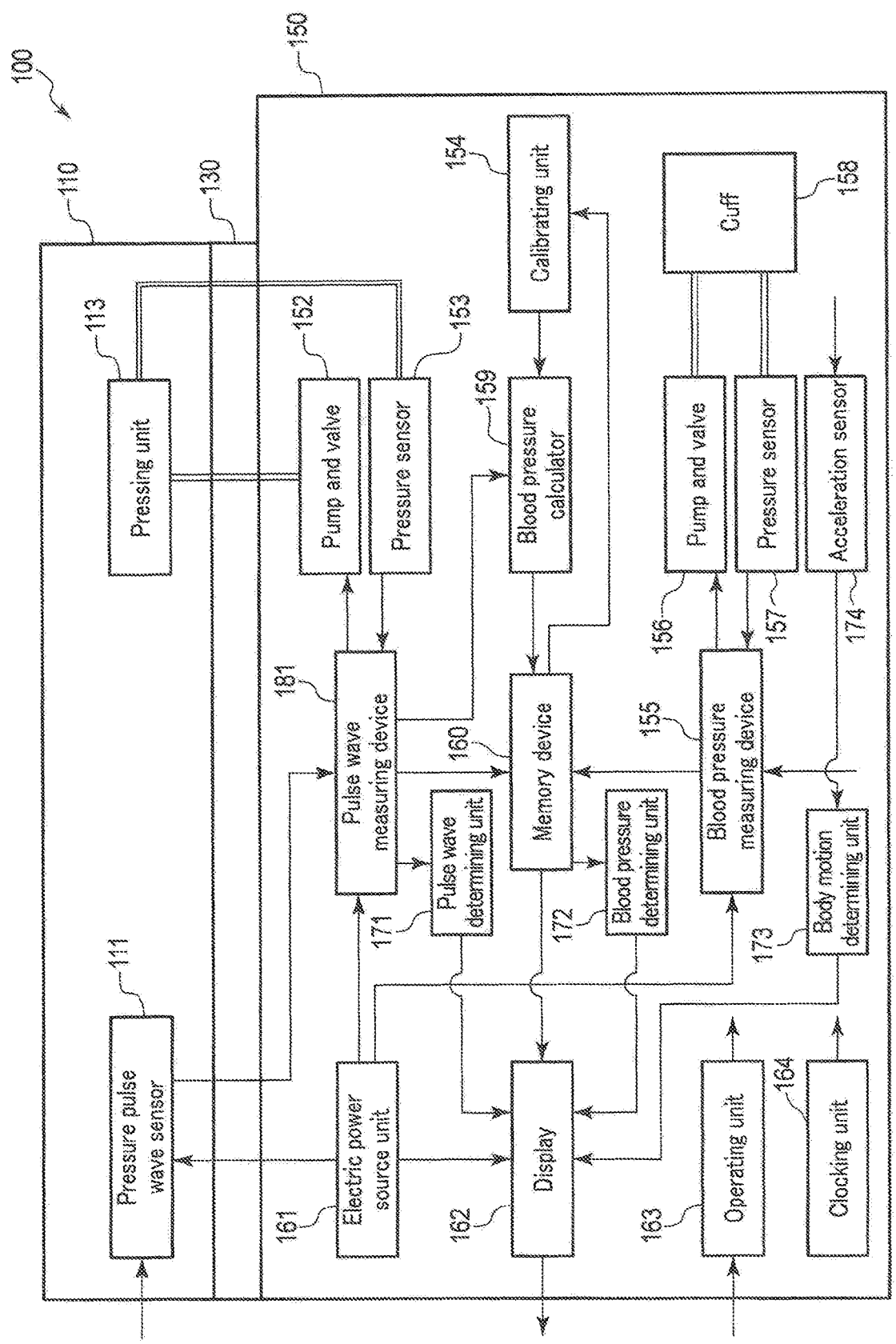
FIG. 1 is a block diagram showing an integral-type blood pressure measuring apparatus according to an embodiment.
Figure 2:
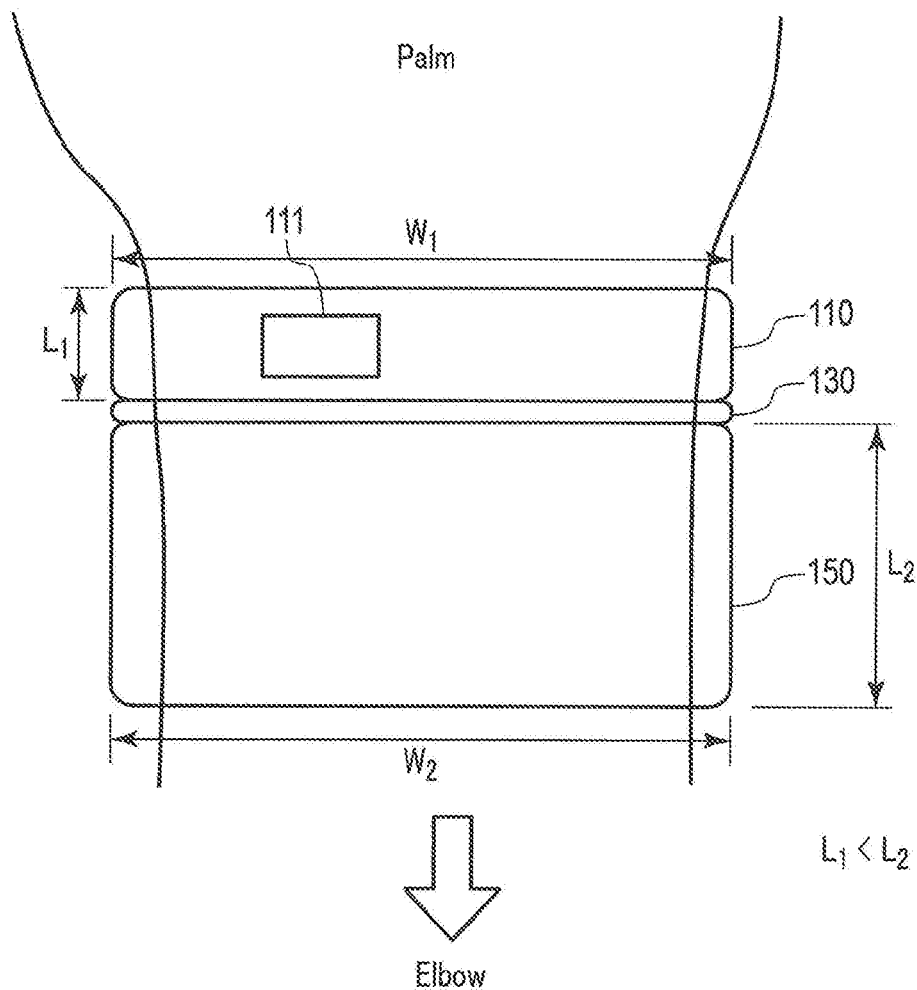
FIG. 2 is an illustration of an example of the blood pressure measuring apparatus of FIG. 1 that is worn around the wrist.
Figure 3:
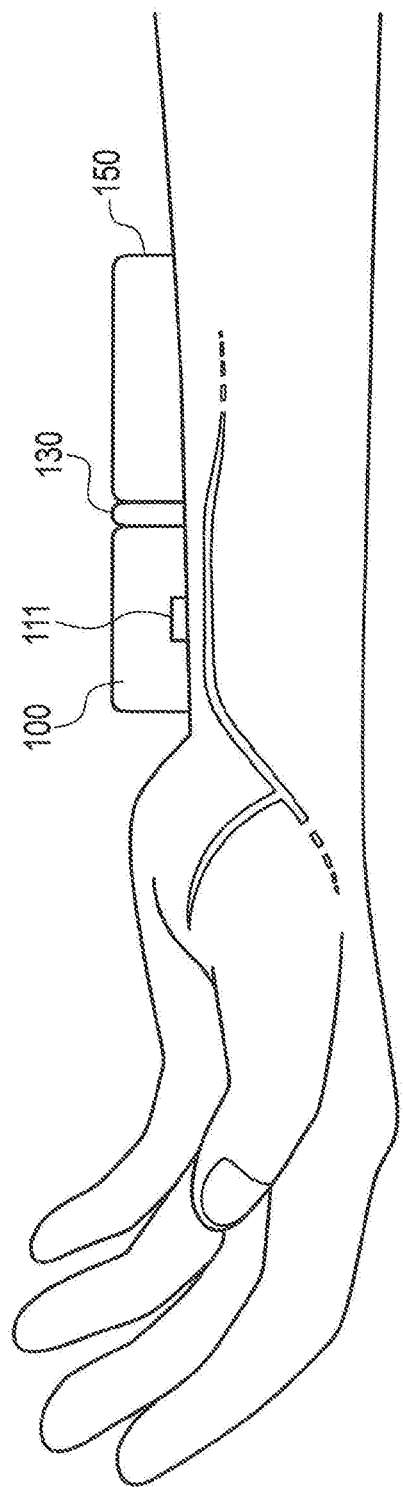
FIG. 3 is an illustration of another example of the blood pressure measuring apparatus of FIG. 1 that is worn around the wrist.

A blood pressure measuring apparatus 100, which is one example of the biological information measuring apparatus according to the present embodiment, will be described with reference to FIGS. 1, 2 and 3. FIG. 1 is a functional block diagram of the blood pressure measuring apparatus 100, showing a pulse wave detector 110 and a blood pressure calibrating device 150 in detail. FIG. 2 is an illustration of one example where the blood pressure measuring apparatus 100 is worn around the wrist and is a schematic perspective view of the example viewed from above the palm. A pressure pulse wave sensor 111 is placed on the wrist side of the pulse wave detector 110. FIG. 3 is an image view of the wearing of the blood pressure measuring apparatus 100 and is a schematic perspective view of the palm viewed from its side (the direction in which the fingers are arranged when the hand is opened). FIG. 3 also shows an example where the pressure pulse wave sensor 111 is placed orthogonally to the radial artery. It is seen from FIG. 3 that the blood pressure measuring apparatus 100 is only put on the arm on the palm side, but in fact the blood pressure measuring apparatus 100 is worn around the arm.

The blood pressure measuring apparatus 100 includes the pulse wave detector 110, a connecting unit 130 and the blood pressure calibrating device 150. The pulse wave detector 110 includes the pressure pulse wave sensor 111 and a pressing unit 113. The blood pressure calibrating device 150 includes a pulse wave measuring device 181, a pump and valve 152, a pressure sensor 153, a calibrating unit 154, a blood pressure measuring device 155, a pump and valve 156, a pressure sensor 157, a cuff 158, a blood pressure calculator 159, a memory device 160, an electric power source unit 161, a display 162, an operation unit 163, a clocking unit 164, a pulse wave determining unit 171, a blood pressure determining unit 172, a body motion determining unit 173 and an acceleration sensor 174. Note that the pulse wave determining unit 171, blood pressure determining unit 172 and body motion determining unit 173 may collectively be referred to as a calibration blood pressure determining unit.

The blood pressure measuring apparatus 100 is annular and is worn around, e.g. a user's wrist like a bracelet to measure user's blood pressure. The pulse wave detector 110 is placed closer to the user's palm than the blood pressure calibrating device 150, as illustrated in FIGS. 2 and 3. In other words, the pulse wave detector 110 is placed in a position farther from the user's elbow than the blood pressure calibrating device 150. In the present embodiment, the pulse wave detector 110 is placed such that the pressure pulse wave sensor 111 is located on the radial artery and accordingly the blood pressure calibrating device 150 is placed closer to the elbow than the pulse wave detector 110. The connecting unit 130 physically connects the pulse wave detector 110 and the blood pressure calibrating device 150 and is made of, e.g. a shock absorber to prevent their measurements from interfering with each other.

The length $L_1$ of the pulse wave detector 110 in the stretching direction of the user's arm is set smaller than the length $L_2$ of the blood pressure calibrating device 150 in the stretching direction. The length $L_1$ of the pulse wave detector 110 in the stretching direction of the arm is set to 40 mm or less and, more ideally, 15 mm to 25 mm. Furthermore, the length $W_1$ of the pulse wave detector 110 in a direction perpendicular to the stretching direction of the arm is set to 4 cm to 5 cm, and the length $W_2$ of the blood pressure calibrating device 150 in a direction perpendicular to the stretching direction is set to 6 cm to 7 cm. Moreover, there is the following relationship between the length $W_1$ and length $W_2$: 0 (or 0.5) cm$<W_2-W_1<$2 cm. With this relationship, $W_2$ is set so as not to be too long to make it difficult to interfere with the surroundings. Since the pulse wave detector 110 falls within such a range, the blood pressure calibrating device 150 is placed closer to the palm, with the result that pulse waves can easily be detected, and the accuracy of measurement can be maintained.

The pressure pulse wave sensor 111 senses pressure pulse waves continuously in terms of time. For example, the pressure pulse wave sensor 111 senses a pressure pulse wave for each beat. The pressure pulse wave sensor 111 is placed on the palm side as shown in FIG. 2 and usually placed in parallel to the stretching direction of the arm as shown in FIG. 3, and includes a plurality of sensors arranged orthogonal to the stretching direction of the arm. The pressure pulse wave sensor 111 can obtain time series data of blood pressure values (blood pressure waveforms) that vary in association with the heartbeat. Note that if the time when the pulse wave measuring device 181 received a pressure pulse wave from the pressure pulse wave sensor 111 is obtained from the clocking unit 164, the time when the pressure pulse wave sensor 111 detected the pressure pulse wave can be estimated.

The pressing unit 113 is an air bag and presses a sensor portion of the pressure pulse wave sensor 111 against the wrist to make it possible to increase the sensitivity of the sensor.

The pulse wave measuring device 181 receives data of pressure pulse waves and time from the pressure pulse wave sensor 111 and sends the data to the memory device 160 and the blood pressure calculator 159. The pulse wave measuring device 181 also drives and controls the pump and valve 152 and the pressure sensor 153 to pressurize or depressurize the pressing unit 113, and adjusts the pressure pulse wave sensor 111 to be pressed against the radial artery of the wrist.

The pump and valve 152 pressurizes or depressurizes the pressing unit 113 in response to an instruction from the pulse wave measuring device 181. The pressure sensor 153 monitors the pressure of the pressing unit 113 and notifies the pulse wave measuring device 181 of the pressure value of the pressing unit 113. Here, the pump and valve 152 and the pressure sensor 153 are placed only in the blood pressure calibrating device 150; however, they can be placed in the pulse wave detector 110 together with a unit for driving and controlling them. In this case, a tube for causing gas to pass therethrough to adjust the pressure need not be provided between the pulse wave detector 110 and the blood pressure calibrating device 150.

The blood pressure measuring unit 155 measures blood pressure that is biological information with higher accuracy than the pressure pulse wave sensor 111. The blood pressure measuring unit 155 measures blood pressure, for example, not continuously but intermittently in terms of time and sends a value of the blood pressure to the calibrating unit 154 via the memory device 160. The blood pressure measuring unit 155 also measures blood pressure using, for example, the oscillometric technique. The blood pressure measuring unit 155 also controls the pump and valve 156 and the pressure sensor 157 and pressurize or depressurize the cuff 158 to measure blood pressure. The blood pressure measuring unit 155 sends systolic blood pressure, time of measurement of the systolic blood pressure, diastolic blood pressure, and time of measurement of the diastolic blood pressure to the memory device 160. Note that the systolic blood pressure will also be referred to as SBP and the diastolic blood pressure will also be referred to as DBP.

The memory device 160 acquires and stores data of pressure pulse waves and the detection time sequentially from the pulse wave measuring device 181 and acquires and stores the SBP, the SBP measurement time, the DBP and the DBP measurement time from the blood pressure measuring unit 155 when the measuring unit is operated.

The calibrating unit 154 acquires, from the memory device 160, the SBP and DBP measured with their measurement time by the blood pressure measuring unit 155 and the data of pressure pulse waves measured with their measurement time by the pulse wave measuring device 181. The calibrating unit 154 calibrates the pressure pulse waves from the pulse wave measuring device 181 based on the blood pressure values from the blood pressure measuring unit 155. Some calibration techniques performed by the calibrating unit 154 are considered and will be described in detail later with reference to FIG. 6.

The blood pressure calculator 159 receives a calibration technique from the calibrating unit 154 to calibrate the pressure pulse wave data from the pulse wave measuring device 181 and store, in the memory device 161, blood pressure data, which is obtained from the pressure pulse wave data, together with the measurement time.

The electric power source unit 161 supplies power to each of the pulse wave detector 110 and the blood pressure calibrating device 150.

The display 162 displays blood pressure measurement results and displays a variety of information items to the user. For example, the display 162 receives data from the memory device 160 and displays the contents of the data. For example, the display 162 displays the pressure pulse wave data with the measurement time. Here, the display 162 is placed only in the blood pressure calibrating device 150, but the display 162 may be placed in the pulse wave detector 110. In this case, for example, in the pulse wave detector 110, the measured blood pressure values are displayed in real time, and in the blood pressure calibrating device 150, a blood pressure value at the time of the last calibration is displayed and the capacity of the current power supply is displayed. As a result, the user is able to obtain a lot of information from the display.

The operation unit 163 receives an operation from the user. The operation unit 163 includes, for example, an operation button for causing the blood pressure measuring unit 155 to start measurement and an operation button for performing calibration. Here, the operation unit 163 is placed only in the blood pressure calibrating device 150, but the operation unit 163 may be placed in the pulse wave detector 110.

The clocking unit 164 generates time and supplies it to a unit that requires the generated time. For example, the memory device 160 records time together with data to be stored.

The calibration blood pressure determining unit determines whether the measurement result of the blood pressure calibrating device 150 for calibration is normal. The calibration blood pressure determining unit may include at least one of the pulse wave determining unit 171, blood pressure determining unit 172 and body motion determining unit 173.

The pulse wave determining unit 171 receives a pulse wave from the pulse wave measuring device 181 to determine whether the pulse wave is irregular during a certain period of time ($P_2$). The fact that the pulse wave is irregular means that the pulse wave is not regular and specifically the physical quantity of the pulse wave is not regular in terms of time. In the present embodiment, for example, when a pulse wave disappears during a period of time, the pulse wave is considered to be irregular. More specifically, when the amplitude of a pulse wave is zero or almost zero during a certain period of time, the pulse wave is considered to be irregular. In the actual device, a pulse wave is considered to be irregular when the amplitude of the pulse wave becomes smaller than a threshold value during a period of time and when the conditions that the threshold value is significantly smaller than the amplitude and a period during which the amplitude is smaller than a threshold value is longer than a certain period of time are satisfied. This threshold value is set to, for example, half or ⅓ of the amplitude.

On receiving a blood pressure value, which is obtained from the calibrated pulse wave, for each beat from the memory device 160, the blood pressure determining unit 172 determines whether the blood pressure value varies during a certain period of time ($P_3$). The variation of the blood pressure value means that the blood pressure value does not fall within a certain range during a certain period of time. In the present embodiment, for example, it is observed whether the amplitude of a pulse wave, SBP and DBP are each increased or decreased from the last beat during a period of time. When the increase or decrease exceeds a threshold value, it is defined that a blood pressure value varies. Alternatively, for example, an average value is obtained for each of the amplitude of a pulse wave, SBP and DBP before the pulse wave determining unit 171 determines whether the pulse waves are irregular. When the amplitude of a pulse wave, SBP and DBP are significantly increased or decreased from their respective average values during which the pulse wave determining unit 171 determines the pulse waves, it is defined that a blood pressure value varies.

The acceleration sensor 174 measures the acceleration of the blood pressure calibrating device 150 and outputs time and the acceleration at the time (i.e. outputs time series data of the acceleration). The acceleration sensor 174 measures the acceleration with respect to, for example, three axes to obtain time series data of the acceleration.

The body motion determining unit 173 receives the time series data of the acceleration from the acceleration sensor 174 to determine whether a body motion is generated during a certain period of time ($P_1$). In the present embodiment, the fact that a body motion is generated means that the acceleration is greater than a threshold value during a certain period of time. In the present embodiment, for example, time series data of the acceleration for three axes of the acceleration sensor 174 is obtained, and when the acceleration for one or more axes of the acceleration sensor 174 is greater than the threshold value, it is defined that a body motion is generated.

The outputs of the pulse wave determining unit 171, blood pressure determining unit 172 and body motion determining unit 173 may be displayed on the display 162. In addition, the determination of the pulse wave determining unit 171, blood pressure determining unit 172 and body motion determining unit 173 is used to control the calibrating operation as shown in FIG. 8 later.

When the pulse wave measuring device 181, calibrating unit 154, blood pressure calculator 159, blood pressure measuring device 155, pulse wave determining unit 171, blood pressure determining unit 172 and body motion determining unit 173, described so far, are implemented, for example, a program for executing the foregoing operation is stored in a secondary storage device included in each of the units, and the central processing unit (CPU) reads the program to execute an operation. Note that the secondary storage device is, for example, a hard disk and may be any device that can store the program, such as a semiconductor memory, a magnetic storage device, an optical storage device, a magneto-optical disk, and a storage device using the phase-change recording technology.

Figure 4:
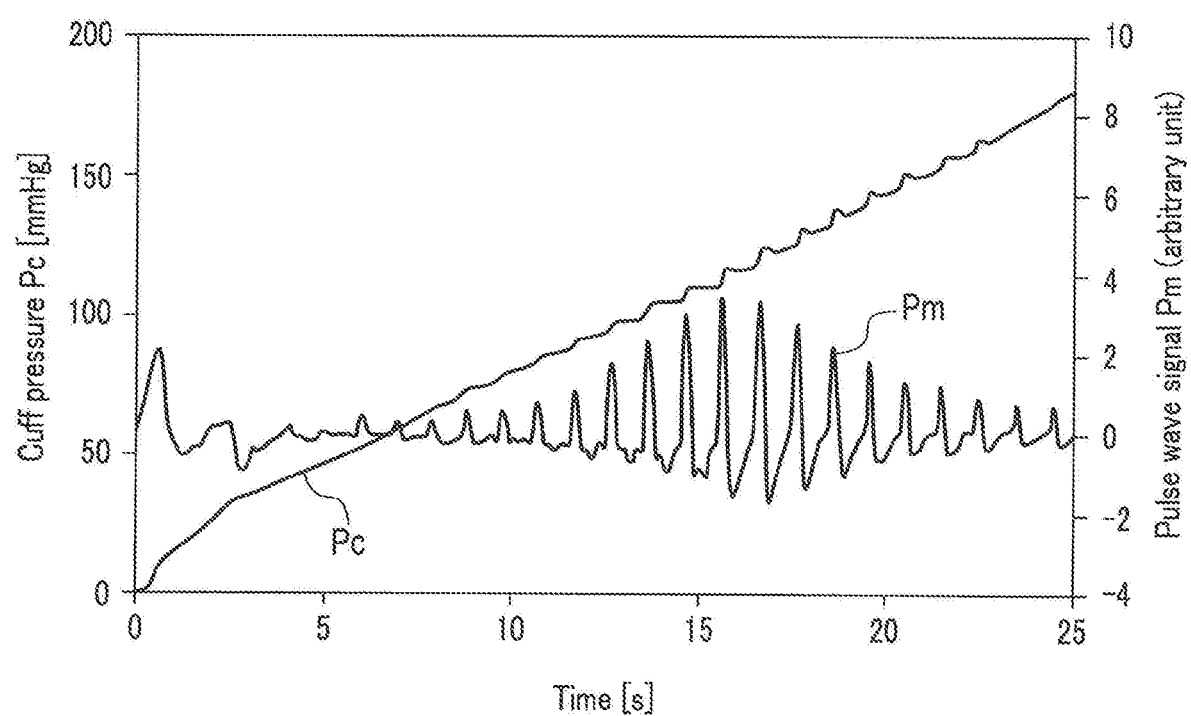
FIG. 4 is a graph showing cuff pressure and pulse wave signal varying with the passage of time in the oscillometric technique.
Figure 5:
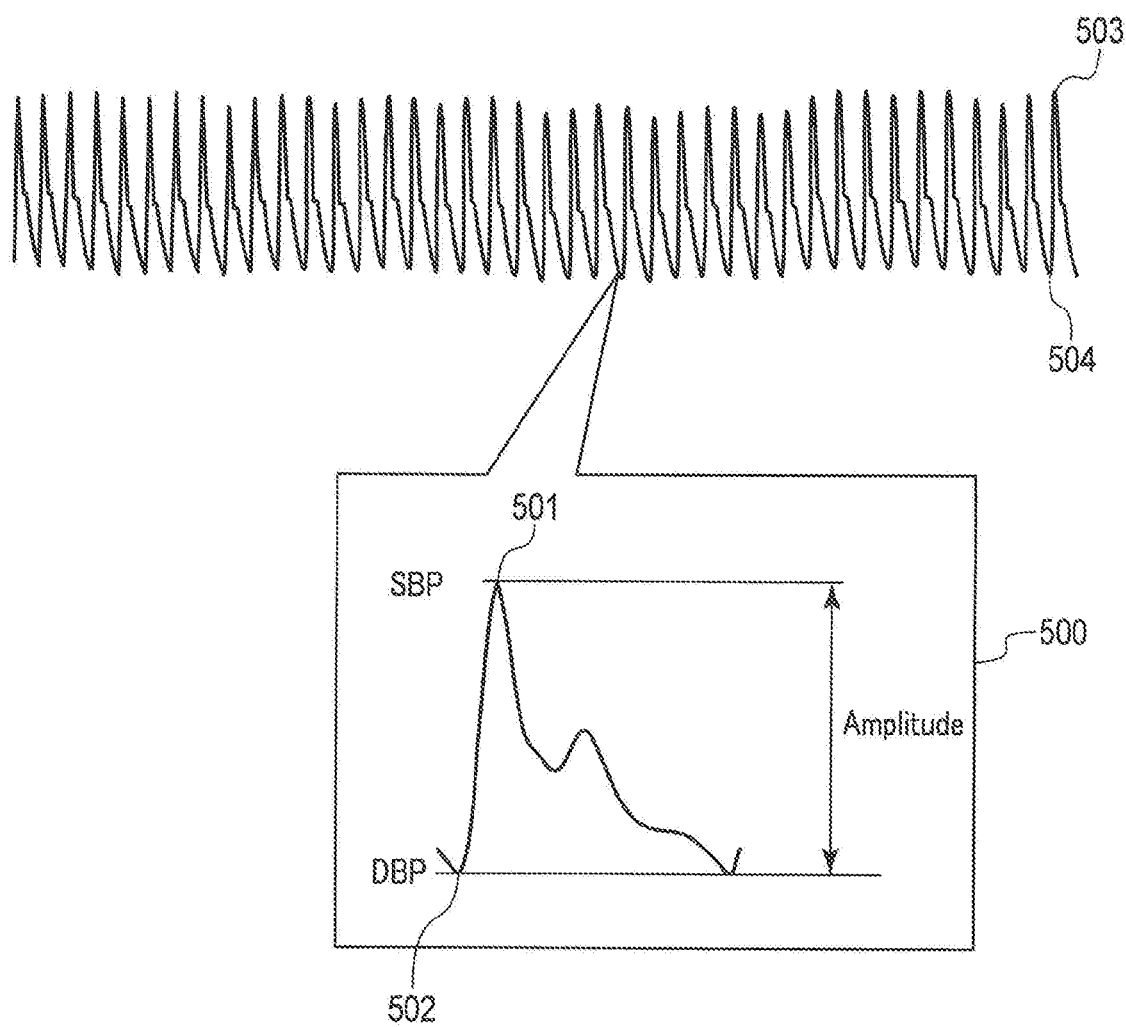
FIG. 5 is a diagram showing pulse pressure varying for each beat with the passage of time and one pulse wave.

The contents of the pulse wave measuring device 181 and blood pressure measuring unit 155 before the calibration unit 154 performs calibration will be described next with reference to FIGS. 4 and 5. FIG. 4 shows variations of cuff pressure and pulse wave signal with the passage of time in the oscillometric blood pressure measurement. FIG. 4 shows variations of cuff pressure and pulse wave signal with the passage of time, and shows that the cuff pressure increases with time and the pulse wave signal gradually increases with the increase in cuff pressure and gradually decreases after its value becomes the maximum. FIG. 5 shows time series data of pulse pressure measured for each beat. FIG. 5 also shows the waveform of one pressure wave.

First, an operation of the blood pressure measuring unit 155 to measure blood pressure by the oscillometric technique will be briefly described with reference to FIG. 4. The calculation of a blood pressure value may be performed in a depressurization process as well as a pressurization process, but here only the pressurization process will be described.

When a user instructs the blood pressure measuring unit 155 to measure blood pressure by the oscillometric technique using the operation unit 163 provided in the blood pressure calibrating device 150, the blood pressure measuring unit 155 starts the operation to initialize a memory area for processing. The blood pressure measuring unit 155 closes the pump of the pump and valve 156 and opens the valve thereof to exhaust air from the cuff 158. Then, it sets the current output value of the pressure sensor 157 as a value corresponding to atmospheric pressure (0 mmHg adjustment).

Then, the blood pressure measuring unit 155 operates as a pressure controller to close the valve of the pump and valve 156, then drive the pump and supply air to the cuff 158. Accordingly, the cuff 158 is expanded and pressurized with a gradual increase in the cuff pressure (Pc in FIG. 4). In this pressurization process, in order to calculate a blood pressure value, the blood pressure measuring unit 155 uses the pressure sensor 157 to monitor the cuff pressure Pc and acquire a variation component of the arterial volume generated in the radial artery of the user's wrist to be measured as a pulse wave signal Pm as shown in FIG. 4.

Then, the blood pressure measuring unit 155 tries to calculate a blood pressure value (SBP and DBP) using a known algorithm through the oscillometric technique, based on the pulse wave signal Pm acquired at this time. When no blood pressure value can be calculated because of data shortage at this time, the same pressurization process as described above is repeated unless the cuff pressure Pc reaches the upper limit pressure (which is preset to, for example, 300 mmHg for safety (correctly this value is a pressurization value)).

If a blood pressure value can be calculated as described above, the blood pressure measuring unit 155 stops the pump of the pump and valve 156 and opens the valve thereof to exhaust air from the cuff 158. Finally, the measurement results of the blood pressure value are sent to the calibrating unit.

Measuring a pulse wave for each beat by the pulse wave measuring device 181 will be described next with reference to FIG. 5. The pulse wave measuring device 181 measures a pulse wave by, for example, the tonometry method.

The Pulse wave measuring device 181 controls the pump and valve 152 and the pressure sensor 153 so that the predetermined pressing pressure becomes the optimum to achieve the optimum measurement by the pressure pulse wave sensor 111, and increases the internal pressure of the pressing unit 113 to the optimum pressing pressure and maintains it. Then, when the pressure pulse wave sensor 111 senses a pressure pulse wave, the pulse wave measuring device 181 acquires the pressure pulse wave.

A pressure pulse wave is detected for each beat as a waveform as shown in FIG. 5, with the result that pressure pulse waves are detected continuously. The pressure pulse wave 500 shown in FIG. 5 is a pressure pulse wave for one beat, and the pressure value indicated by numeral 501 corresponds to SBP and the pressure value indicated by numeral 502 corresponds to DBP. As represented by the time-series pressure pulse waves in FIG. 5, SBP 503 and DBP 504 usually vary for each pressure pulse wave.

Figure 6:
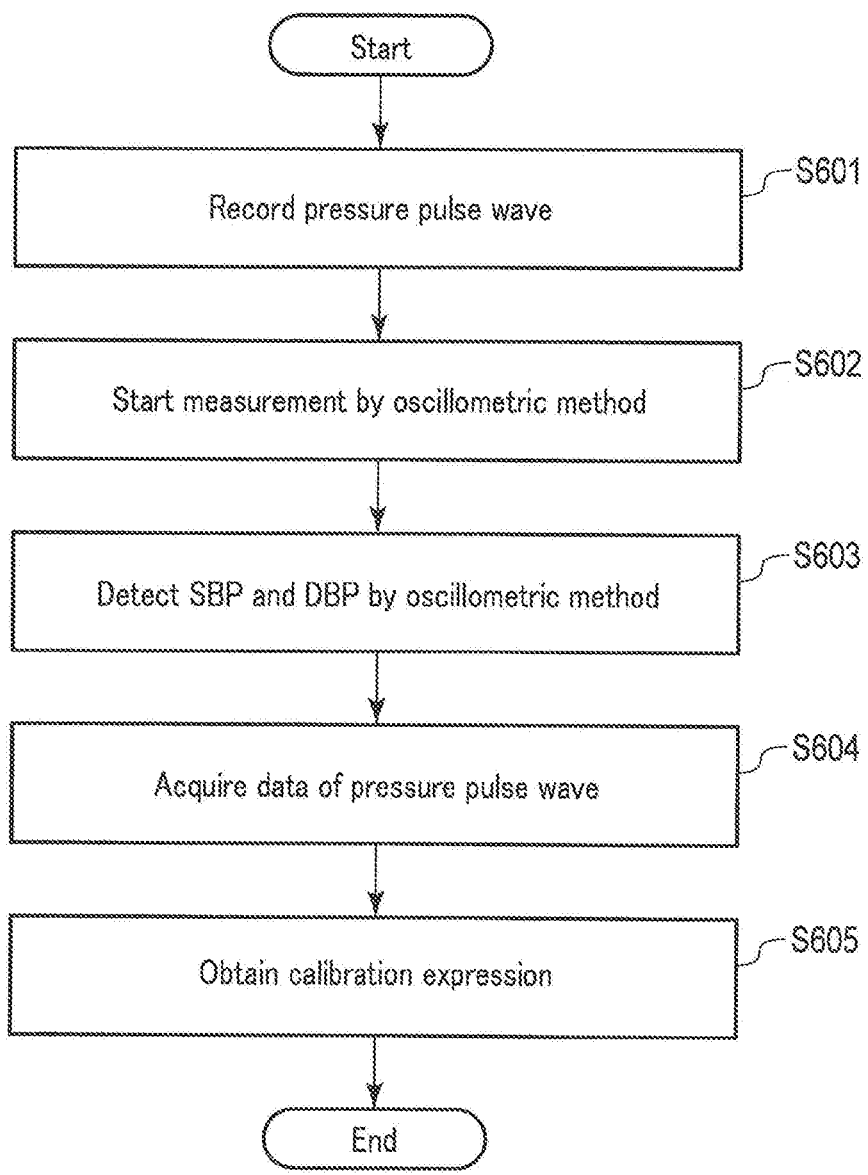
FIG. 6 is a flowchart showing a first calibration method.

The operation of the calibrating unit 154 will be described next with reference to FIG. 6.

The calibrating unit 154 calibrates the pressure pulse wave detected by the pulse wave measuring device 181 using the blood pressure value measured by the blood pressure measuring unit 155. That is, the calibrating unit 154 determines the blood pressure value of the maximum value 501 and the minimum value 502 of the pressure pulse wave detected by the pulse wave measuring device 181.

(Calibration Method)

The pulse wave measuring device 181 starts to record pressure pulse wave data of the pressure pulse wave and store the pressure pulse wave data in sequence in the memory device 160 (step S601). After that, for example, the user activates the blood pressure measuring unit 155 using the operation unit 163 and starts measurement by the oscillometric technique (step S602). The blood pressure measuring unit 155 records SBP data and DBP data of SBP and DBP detected by the oscillometric technique, based on the pulse wave signal Pm and stores the SBP data and DBP data in the memory device 160 (step S603).

The calibrating unit 154 acquires pressure pulse waves corresponding to the SBP data and DBP data from the pressure pulse wave data (step S604). The calibrating unit 154 obtains a calibration expression based on the maximum value 501 of the pressure pulse wave corresponding to the SBP and the minimum value 502 of the pressure pulse wave corresponding to the DBP (step S605).

(Separation Type)

Figure 7:
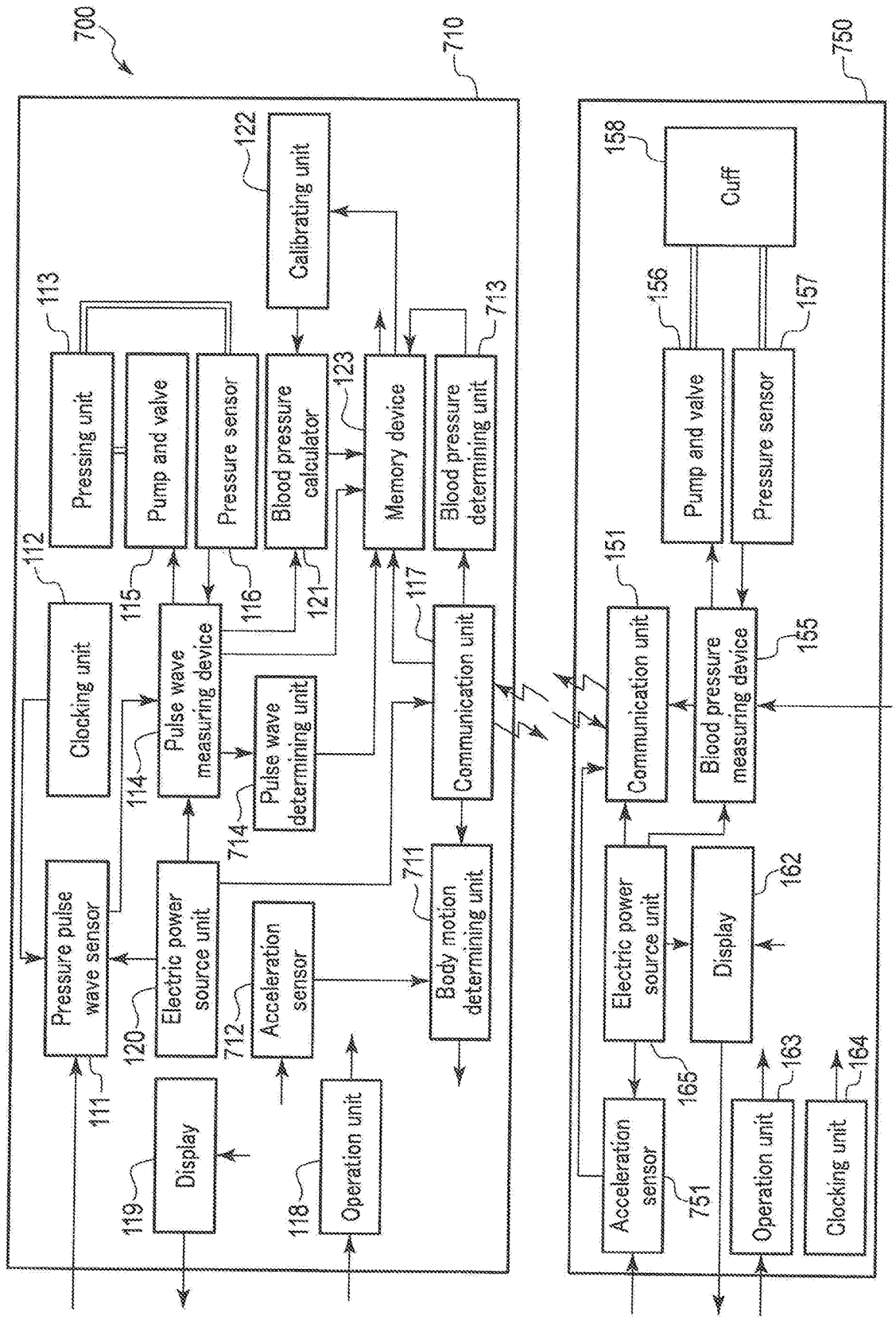
FIG. 7 is a block diagram showing a discrete-type blood pressure measuring apparatus according to an embodiment.

A blood pressure measuring apparatus 700, which is one example of the biological information measuring apparatus according to the present embodiment, will be described with reference to FIGS. 7, 2 and 3. FIG. 7 is a functional block diagram of the blood pressure measuring apparatus 700 in which a sensing apparatus 710 and a calibrating apparatus 750 are separated, showing the sensing apparatus 710 and calibrating apparatus 750 in detail. FIG. 2 is an illustration of one example where the blood pressure measuring apparatus 100 is worn around the wrist and is a schematic perspective view of the example viewed from above the palm, and the same holds true for the blood pressure measuring apparatus 700, excluding the connecting unit 130 shown in FIGS. 2 and 3. A pressure pulse wave sensor 111 is placed on the wrist side of the sensing apparatus 710. FIG. 3 is an image view of the wearing of the blood pressure measuring apparatus 100 and is a schematic perspective view of the palm viewed from its side (the direction in which the fingers are arranged when the hand is opened), and the same holds true for the blood pressure measuring apparatus 700, excluding the connecting unit 130 shown in FIGS. 2 and 3. FIG. 3 also shows an example where the pressure pulse wave sensor 111 is placed orthogonally to the radial artery. It is seen from FIG. 3 that the blood pressure measuring apparatus 700 is only put on the arm on the palm side, but in fact the blood pressure measuring apparatus 700 is worn around the arm. With respect to FIGS. 2 and 3, the separation type is similar to the integration type.

The blood pressure measuring apparatus 700 includes the sensing apparatus 710 and calibrating apparatus 750. The sensing apparatus 710 includes a pressure wave sensor 111, a clocking unit 112, a pressing unit 113, a pulse wave measuring device 114, a pump and valve 115, a pressure sensor 116, a communication unit 117, an operation unit 118, a display 119, an electric power source unit 120, a blood pressure calculator 121, a calibrating unit 122, a memory device 123, a body motion determining unit 711, an acceleration sensor 712, a blood pressure determining unit 713, and a pulse wave determining unit 714. The calibrating apparatus 750 includes an electric power source unit 165, a blood pressure measuring unit 155, a pump and valve 156, a pressure sensor 157, a cuff 158, a display 162, an operation unit 163, a clocking unit 164, a communication unit 151, and an acceleration sensor 751.

The blood pressure measuring apparatus 700 is annular and is worn around, e.g. a user's wrist like a bracelet to measure user's blood pressure from biological information. The sensing apparatus 710 is placed closer to the user's palm than the calibrating apparatus 750, as illustrated in FIGS. 2 and 3. In other words, the sensing apparatus 710 is placed in a position farther from the user's elbow than the calibrating apparatus 750. In the present embodiment, the sensing apparatus 710 is placed such that the pressure pulse wave sensor 111 is located on the radial artery and accordingly the calibrating apparatus 750 is placed closer to the elbow than the sensing apparatus 710. In addition, the sensing apparatus 710 and the calibrating apparatus 750 can be put on different arms. It is preferable that the sensing apparatus 710 and the calibrating apparatus 750 be usually placed on the same level. It is also preferable that the sensing apparatus 710 and the calibrating apparatus 750 be aligned with the heart.

The length $L_1$ of the sensing apparatus 710 in the stretching direction of the user's arm is set smaller than the length $L_2$ of the calibrating apparatus 750 in the stretching direction. The length $L_1$ of the sensing apparatus 710 in the stretching direction of the arm is set to 40 mm or less and, more preferably, 15 mm to 25 mm. Furthermore, the length $W_1$ of the pulse wave detector 110 in a direction perpendicular to the stretching direction of the arm is set to 4 cm to 5 cm, and the length $W_2$ of the calibrating apparatus 750 in a direction perpendicular to the stretching direction is set to 6 cm to 7 cm. Moreover, there is the following relationship between the length $W_1$ and length $W_2$: 0 (or 0.5) cm<$W_2$−$W_1$<2 cm. With this relationship, $W_2$ is set so as not to be too long to make it difficult to interfere with the surroundings. Since the sensing apparatus 710 falls within such a range, the calibrating apparatus 750 is placed closer to the palm, with the result that pulse waves can easily be detected, and the accuracy of measurement can be maintained. However, the calibrating apparatus 750 may be put on the arm for measurement.

The pressure pulse wave sensor 111, clocking unit 112 and pressing unit 113 are similar to the pulse wave detector 110 of the integration type shown in FIG. 1. Since the sensing apparatus 710 of the separation type is separated from the calibrating apparatus 750, the pump and valve 115 and pressure sensor 116 for operating the pressing unit 113 need to be provided in the sensing apparatus 710. The pulse wave measuring device 114 for controlling the pump and valve 115 and pressure sensor 116 also need to be provided in the sensing apparatus 710. The electric power source unit 120 also need to be provided in the sensing apparatus 710. In addition, the operation unit 118 and display 119 may be provided in the sensing apparatus 710.

The display 119 also displays blood pressure measurement results and displays a variety of information items to the user. For example, the display 119 receives data from the pulse wave measuring device 114 and displays the contents of the data. For example, the display 119 displays the pressure pulse wave data with the measurement time.

The communication units 117 and 151 communicate to each other by a communication system capable of exchanging data at close range. These communication units employ, for example, a close-range wireless communication system. Specifically, the communication system includes Bluetooth (registered trademark), TransferJet (registered trademark), ZigBee (registered trademark), IrDA (registered trademark) and the like.

The pump and valve 115 pressurizes or depressurizes the pressing unit 113 in response to an instruction from the pulse wave measuring device 114. The pressure sensor 116 monitors the pressure of the pressing unit 113 and notifies the pulse wave measuring device 114 of the pressure value of the pressing unit 113.

The electric power source unit 120 supplies power to each unit of the sensing apparatus 710.

The acceleration sensor 712 measures the acceleration of the sensing apparatus 710 and outputs time and the acceleration at the time. Like the acceleration sensor 751, the acceleration sensor 712 measures the acceleration with respect to, for example, x, y and z axes of three spaces axes to obtain time series data of the acceleration.

The operation unit 118 receives an operation from the user. The operation unit 118 includes, for example, an operation button for causing the pulse wave measuring device 114 to start measurement and an operation button for starting or stopping communications.

The memory device 123 acquires and stores data of pressure pulse waves and the detection time sequentially from the pulse wave measuring device 114 of the sensing apparatus 710, and acquires and stores the SBP, the SBP measurement time, the DBP and the DBP measurement time from the blood pressure measuring unit 155 when the measuring unit is operated. In addition, the memory device 123 records type information and (or) unique identification information of the calibrating apparatus that is a measuring device of first biological information (measured by the blood pressure measuring device 155) for calibration used for calculation of the measured biological information (continuous blood pressure) in association with the measured biological information. It is therefore possible to know which blood pressure monitor (type and unique number of the device) was used for calibration from the measured biological information.

The blood pressure calculator 121 receives a calibration technique from the calibrating unit 122 to calibrate the pressure pulse wave data from the pulse wave measuring device 114 and store, in the memory device 123, blood pressure data, which is obtained from the pressure pulse wave data, together with the measurement time.

The electric power source unit 165 supplies power to each unit of the calibrating apparatus 750.

The operation unit 163 receives an operation from the user. The operation unit 163 includes, for example, an operation button for causing the blood pressure measuring device 155 to start measurement and an operation button for performing calibration, and an operation button for starting or stopping communications.

The clocking unit 164 generates time and supplies it to a unit that requires the generated time.

The pulse wave determining unit 714 receives a pulse wave from the pulse wave measuring device 114. In other respects, the pulse wave determining unit 714 is similar to the pulse wave determining unit 171 of the integral type.

The blood pressure determining unit 713 is similar to the blood pressure determining unit 172 of the integral type.

The acceleration sensor 751 measures the acceleration of the calibrating apparatus 750 and outputs time and the acceleration at the time (i.e. outputs time series data of the acceleration). Like the acceleration sensor 712, the acceleration sensor 751 measures the acceleration with respect to three axes to obtain time series data of the acceleration.

The body motion determining unit 711 receives the time series data of the acceleration from each of the acceleration sensors 751 and 712 to determine whether a body motion is generated during a certain period of time ($P_1$). In the present embodiment, the fact that a body motion is generated means that the acceleration is greater than a threshold value during a certain period of time. In the present embodiment, for example, time series data of the acceleration for three axes of each of the acceleration sensors 751 and 712 is obtained, and when the acceleration for one or more axes of each of the acceleration sensors 751 and 712 is greater than the threshold value, it is defined that a body motion is generated. The axis on which the acceleration becomes larger than the threshold value may vary between the acceleration sensor 751 and the acceleration sensor 712. Instead of using the values of the acceleration sensors 751 and 712, the value of only one of the acceleration sensors may be used and, in this case, the other acceleration sensor need not be provided.

When the pulse wave measuring device 114, calibrating unit 122, blood pressure calculator 121 and blood pressure measuring device 155 described so far, are implemented, for example, a program for executing the foregoing operation is stored in a secondary storage device included in each of the units, and the central processing unit (CPU) reads the program to execute an operation. Note that the secondary storage device is, for example, a hard disk and may be any device that can store the program, such as a semiconductor memory, a magnetic storage device, an optical storage device, a magneto-optical disk, and a storage device using the phase-change recording technology.

The programs for executing the operations of the pulse wave measuring device 114, calibrating unit 122, blood pressure calculator 121, blood pressure measuring device 155, body motion determining unit 711, blood pressure determining unit 713 and pulse wave determining unit 714 may be stored in, e.g. a server other than the sensor device and the calibrating device, and may be executed therein. In this case, the pulse wave data measured by the sensor device and the blood pressure data that is the biological information measured by the calibrating device are transmitted to the server and calibrated therein, with the result that the server can obtain blood pressure from the pulse wave. Since, in this case, the processing is performed by the server, the processing speed is likely to increase. Since, furthermore, the device portions of the pulse wave measuring device 114, calibrating unit 122, blood pressure calculator 121 and blood pressure measuring device 155 are removed from the sensor device and the calibrating device, they are decreased in size and thus can be easily disposed at positions where sensing can be performed accurately. As a result, the burden on the user is reduced and accordingly blood pressure can be measured easily and accurately.

An operation of determining each of the continuation, suspension and resumption of calibrating operation performed when blood pressure is measured for the calibration (using the oscillometric technique) by operating the blood pressure measuring unit 155 of the blood pressure calibrating device 150 and the calibrating apparatus 750 will be described with reference to FIG. 8. The calibrating operation means an operation in which the blood pressure measuring unit 155 measures blood pressure for calibration. FIG. 8 shows the operations performed by the pulse wave determining unit 171, blood pressure determining unit 172 and body motion determining unit 173 provided in the blood pressure calibrating device 150 shown in FIG. 1 and the operations performed by the body motion determining unit 711, blood pressure determining unit 713 and pulse wave determining unit 714 provided in the sensing apparatus 710. These determining units may be provided in the sensing apparatus 710 or the calibrating apparatus 750. Alternatively, a server device outside the blood pressure measuring apparatus 700 is supplied with necessary information to execute a program for performing the procedure shown in FIG. 8.

First, when the blood pressure measuring device 155 detects that blood pressure measurement for calibration is started, the acceleration sensors 751 and 712 (or the acceleration sensor 174, the following parenthesized terms represent the portions corresponding to the first embodiment) detect acceleration and send the acceleration to the body motion determining unit 711 (step S801). The body motion determining unit 711 (or the body motion determining unit 173) determines whether or not the acceleration is smaller than a threshold value ($TH_1$) during a prescribed period ($P_1$) (step S802).

When the body motion determining unit 711 determines that the acceleration is smaller than $TH_1$, the calibrating operation is continued, and the pulse wave determining unit 714 (pulse wave determining unit 171) detects a pulse wave (step S803). The pulse wave determining unit 714 (pulse wave determining unit 171) determines whether the pulse wave is not irregular during a prescribed period ($P_2$) (step S804). When the pulse wave determining unit 714 (pulse wave determining unit 171) determines that the pulse wave is not irregular, the calibrating operation is continued, and the blood pressure determining unit 713 (blood pressure determining unit 172) receives a blood pressure value based on the pulse wave for each beat from the memory device 123 (memory device 160) (step S805). The blood pressure determining unit 713 (blood pressure determining unit 172) determines whether the blood pressure value does not vary during a prescribed period ($P_3$) (step S806). When the blood pressure determining unit 713 (blood pressure determining unit 172) determines that the blood pressure value does not vary, the calibrating operation is continued (step S807).

On the other hand, when the body motion determining unit 711 determines in step S802 that the acceleration is larger than the threshold value $TH_1$ during the prescribed period $P_1$ and body motion is generated, or when it determines in step S804 that the pulse wave is irregular during the prescribed period $P_2$, or when it determines in step S806 that the blood pressure value varies during the prescribed period $P_3$, the process proceeds to step S809 and the calibrating operation is suspended (step S809). After a prescribed period ($P_0$), the calibrating operation is resumed (step S810), and the process returns to step S801. When the body motion determining unit 711 does not determine that the calibrating operation has been terminated, the process returns to step S801. When it determines that the calibrating operation has been terminated, this operation ends.

Steps S802, S804 and S806 are not executed at the same time. For example, steps S801, S803 and S805 may be executed during the same period and almost simultaneously the determination of steps 802, 804 and 806 may be performed.

Note that the foregoing flowchart is merely an example. For example, the flow may proceed to step S807 when YES is obtained in one of steps S802, S804 and S806.

When the blood pressure measuring unit 155 determines that blood pressure can be measured (OK) in the step of FIG. 8 before it starts the measurement (step S807), it may start the measurement. When it determines that blood pressure cannot be measured (NO) in any of steps S802, S804 and S806, it does not start (or it suspends) the measurement but may retry the measurement after certain time elapses.

In addition, when the blood pressure measuring unit 155 produces a measurement result, it determines the measurement result as "NG" as a calibration value based on at least one of the pressure pulse wave information, the acceleration signal and, in some cases, the variation information of the blood pressure measuring unit 155 under measurement (NO is obtained in one of steps S802, S804 and S806), it does not use it as a calibration value but may retry the measurement after certain time elapses.

According to the embodiment described above, in the integral type, the biological information measuring apparatus is compacted by the pulse wave detector that detects pulse waves continuously in terms of time, the blood pressure measuring unit that measures biological information (first biological information) intermittently, and the connecting unit into which the pulse wave detector and the blood pressure measuring unit are physically integrated. Thus, the biological information measuring apparatus can easily perform measurement and is highly convenient for the user. Since, furthermore, the calibrating apparatus calibrates a pulse wave based on the biological information measured by the blood pressure measuring unit, it can calculate the biological information from the pulse wave with high accuracy, and the user can easily obtain high-accuracy biological information. In addition, since the blood pressure measuring unit only measures the biological information intermittently, the time for the blood pressure measuring unit to interfere with the user is shortened.

On the other hand, in the separation type, since the sensing apparatus and the calibrating apparatus are separated from each other, the alignment of the calibrating apparatus need not be considered, and the pressure pulse wave sensor of the sensing apparatus can be placed in the optimum position. Since the pulse wave is calibrated by the first blood pressure value measured by the calibrating apparatus and the second blood pressure value is calculated from the pulse wave, high-accuracy biological information can be calculated from the pulse wave, and the user can easily obtain the high-accuracy biological information. Since, furthermore, the calibrating apparatus is also independent, it can be located to easily perform calibration without depending on the placement of the sensing apparatus. Since the sensing apparatus and the calibrating apparatus each include an acceleration sensor and a barometric pressure sensor and their time histories are compared to know the histories of motion and height of the sensing apparatus and the calibrating apparatus, the relationship in location between the sensing apparatus and the calibrating apparatus can be estimated. As a result, it can be determined whether the sensing apparatus and the calibrating apparatus can properly be attached.

In addition, the determination during the calibrating operation of the present embodiment makes it possible to eliminate as many noise components as possible in calibrating body motion, irregular pulse waves, and varying blood pressure. As a result, desirable blood pressure calibration can be achieved correctly.

In the embodiment described above, the pressure pulse wave sensor 111 detects, for example, a pressure pulse wave of the radial artery passing through a portion to be measured (e.g. the left wrist) (tonometry method). However, the invention is not limited to this. The pressure pulse wave sensor 111 may detect the pulse wave of the radial artery passing through a portion to be measured (e.g. the left wrist) as a change in impedance (impedance method). The pressure pulse wave sensor 111 may include a light-emitting element that emits light toward an artery passing through a corresponding portion of the portion to be measured and a light-receiving element that receives reflected light (or transmitted light) of the light to detect the pulse wave of the artery as a change in volume (photoelectric method). The pressure pulse wave sensor 111 may also include a piezoelectric sensor that is in contact with the portion to be measured to detect distortion due to the pressure of the artery passing through the corresponding portion of the portion to be measured as a change in electrical resistance (piezoelectric method). The pressure pulse wave sensor 111 may also include a transmitting element that transmits a radio wave (transmission wave) toward an artery passing through the corresponding portion of the portion to be measured and a receiving element that receives a reflected wave of the radio wave to detect a change in the distance between the artery and the sensor due to the pulse wave of the artery as a phase shift between the transmission wave and the reflected wave (radio wave irradiation method). If a physical quantity capable of calculating blood pressure can be observed, a method other than the foregoing methods may be applied.

Furthermore, it is assumed in the foregoing embodiment that the blood pressure measuring apparatus 100 is put on the left wrist as a portion to be measured, but this invention is not limited thereto. For example, it may be put on the right wrist. The portion to be measured has only to include an artery and may be an upper limb such as an upper arm other than the wrist or an lower limb such as an ankle and a thigh.

The apparatus of the present invention can also be implemented by a computer and a program. The program can be recorded on a recording medium and provided via a network.

In addition, the foregoing apparatuses and their apparatus portions can be implemented by either a hardware configuration or a combination configuration of hardware resources and software. As the software of the combination configuration, a program that is installed in a computer in advance from a network or a computer-readable recording medium and executed by a processor of the computer to cause the computer to fulfill the functions of the respective apparatuses is used.

This invention is not limited to the foregoing embodiments. When the invention is reduced to practice, its structural elements can be modified in different ways and embodied without departing from the spirit of the invention. In addition, a variety of inventions can be made by appropriate combinations of the structural elements of the embodiments. For example, some of the structural elements of the embodiments can be deleted. Furthermore, the structural elements of different embodiments can be combined appropriately.

Part or all of the foregoing embodiments may be described as in the following additional statements, but are not limited thereto.

(Additional Statement 1)

A biological information measuring apparatus including a first hardware processor and a memory, comprising:
  detecting pulse waves continuously in terms of time;
  measuring first biological information intermittently;
  calculating second biological information from the pulse waves based on the first biological information;
  determining whether a result of measurement of the first biological information is normal; and
  suspending the measurement in a case where it is not determined that the result of measurement is normal and resuming the measurement after a lapse of a prescribed period, and continuing the measurement in the other cases,
  wherein the memory includes a memory device that stores the second biological information.

(Additional Statement 2)

A biological information measuring apparatus including a sensing apparatus including a first hardware processor and a calibrating apparatus including a second hardware processor and a memory,
  the first hardware processor being configured to:
  measure first biological information intermittently; and
  transmit data containing the first biological information to the sensing apparatus,
  the second hardware processor being configured to:
  detecting pulse waves continuously in terms of time;
  receiving the first biological information;
  calculating second biological information from the pulse waves based on the first biological information;
  determine whether a result of measurement of the first biological information is normal; and
  suspend the measurement in a case where it is not determined that the result of measurement is normal and resume the measurement after a lapse of a prescribed period, and continue the measurement in the other cases, and
  the memory including a memory device that stores the second biological information.

(Additional Statement 3)

A biological information measuring method comprising:
  detecting pulse waves continuously in terms of time using at least one hardware processor;
  measuring first biological information intermittently using at least one hardware processor;
  calculating second biological information from the pulse waves based on the first biological information using at least one hardware processor; and
  determining whether a result of measurement of the first biological information is normal using at least one hardware processor,
  wherein the measurement is suspended in a case where it is not determined that the result of measurement is normal using at least one hardware processor and resumed after a lapse of a prescribed period, and the measurement is continued in the other cases.

(Additional Statement 4)

A biological information measuring method comprising:
  measuring first biological information intermittently using at least one hardware processor;
  transmitting data containing the first biological information to the sensing apparatus using at least one hardware processor;

detecting pulse waves continuously in terms of time using at least one hardware processor;

receiving the first biological information using at least one hardware processor;

calculating second biological information from the pulse waves based on the first biological information using at least one hardware processor; and determining whether a result of measurement of the first biological information is normal using at least one hardware processor, wherein the measurement is suspended in a case where it is not determined that the result of measurement is normal using at least one hardware processor and resumed after a lapse of a prescribed period, and the measurement is continued in the other cases.

What is claimed is:

1. A biological information measuring apparatus comprising:
    a pulse wave sensor configured to detect pulse waves continuously in terms of time; and
    a processor coupled to a memory, wherein the processor is configured to:
        measure a first blood pressure value as first biological information intermittently;
        calibrate the pulse waves by the first biological information;
        calculate second biological information from the calibrated pulse waves; and
        determine whether a result of measurement of the first biological information is normal based on whether body motion is generated, whether the detected pulse waves are irregular by determining that an amplitude of the detected pulse waves is below a threshold value during a period of time, and whether the measured first blood pressure value varies during the measurement of the first biological information,
    wherein the processor is configured to suspend the measurement and resume the measurement after a lapse of a prescribed period to start a calibration and repeat a suspension of the measurement and the calibration after a lapse of a prescribed period until the calibration is completed in a case where the processor does not determine that the result of the measurement is normal based on at least one of the body motion being generated, the detected pulse waves being irregular, or the measured first blood pressure value varying, and the processor is configured to continue the measurement in other cases where the processor determines that the result of the measurement is normal based on the body motion not being generated, the detected pulse waves not being irregular and the measured first blood pressure value failing to vary, and
    wherein the second biological information indicates a second blood pressure value.

2. A biological information measuring apparatus comprising a sensing apparatus and a calibrating apparatus,
    the calibrating apparatus comprising:
        a first processor configured to measure a first blood pressure value as first biological information intermittently; and
        a transmitter configured to transmit data containing the first biological information to the sensing apparatus,
    the sensing apparatus comprising:
        a pulse wave sensor configured to detect pulse waves continuously in terms of time;
        a receiver configured to receive the first biological information; and
        a second processor coupled to a memory, wherein the second processor is configured to:
            calibrate the pulse waves by the first biological information;
            calculate second biological information from the calibrated pulse waves; and
            determine whether a result of measurement of the first biological information is normal based on whether body motion is generated, whether the detected pulse waves are irregular by determining that an amplitude of the detected pulse waves is below a threshold value during a period of time, and whether the measured first blood pressure value varies during the measurement of the first biological information,
    wherein the first processor is configured to suspend the measurement and resume the measurement after a lapse of a prescribed period to start a calibration and repeat a suspension of the measurement and the calibration after a lapse of a predetermined period until the calibration is completed in a case where the second processor does not determine that the result of the measurement is normal based on at least one of the body motion being generated, the detected pulse waves being irregular, or the measured first blood pressure value varying, and the first processor is configured to continue the measurement in other cases where the second processor determines that the result of the measurement is normal based on the body motion not being generated, the detected pulse waves not being irregular, and the measured first blood pressure value failing to vary, and
    wherein the second biological information indicates a second blood pressure value.

3. The apparatus according to claim 1, further comprising a body motion sensor configured to detect body motion information,
    wherein the processor is configured to:
        determine whether the body motion is generated during a first period of the measurement of the first biological information before the pulse waves are calibrated, based on the body motion information;
        determine whether the detected pulse waves are irregular during a second period of the measurement of the first biological information before the pulse waves are calibrated, based on the pulse waves;
        determine whether the measured first blood pressure value varies during a third period of the measurement of the first biological information before the pulse waves are calibrated, based on the second biological information; and
        continue the measurement when the body motion is not generated during the first period, the detected pulse waves are not irregular during the second period and the measured first blood pressure value fails to vary during the third period.

4. The apparatus according to claim 2, wherein:
    the sensing apparatus further comprises a body motion sensor configured to detect body motion information of the calibrating apparatus;
    the second processor is configured to:
        determine whether the body motion is generated during a first period of the measurement of the first biological information before the pulse waves are calibrated, based on the body motion information;
        determine whether the detected pulse waves are irregular during a second period of the measurement of the first biological information before the pulse waves are calibrated, based on the pulse waves; and determine whether the measured first blood pressure value varies during a third period of the measurement of the first biological information before the pulse waves are calibrated, based on the second biological information; and the first processor is configured to continue the measurement when it is determined that the body motion is not generated during the first period, the detected pulse waves are not irregular during the second period and the measured first blood pressure value fails to vary during the third period.

5. The apparatus according to claim 3, wherein the processor is configured to suspend the measurement when it is determined that the body motion is generated during the first period, it is determined that the detected pulse waves are irregular during the second period or it is determined that the measured first blood pressure value varies during the third period, and the processor resumes the measurement after the lapse of the prescribed period.

6. The apparatus according to claim 3, wherein:

the body motion sensor comprises an acceleration sensor, and the processor is configured to determine that the body motion is generated when acceleration indicated by the acceleration sensor is larger than a first threshold value during the first period;

the processor is configured to determine that the detected pulse waves are irregular when a period during which an amplitude of the detected pulse waves is smaller than a second threshold value is longer than a prescribed period of time during the second period; and the processor is configured to determine that the measured first blood pressure value varies when increase or decrease of each of the amplitude of the detected pulse waves, systolic blood pressure and diastolic blood pressure for each beat exceeds a third threshold value.

7. The apparatus according to claim 1, wherein the processor is configured to measure the first biological information with higher accuracy than the second biological information based on the detected pulse waves detected from the pulse wave sensor.

8. The apparatus according to claim 3, wherein the pulse wave sensor is configured to detect the detected pulse waves for each beat.

9. A biological information measuring method comprising:

detecting pulse waves continuously in terms of time;

measuring a first blood pressure value as first biological information intermittently;

calibrating the pulse waves by the first biological information;

calculating second biological information from the calibrated pulse waves; and determining whether a result of measurement of the first biological information is normal based on whether body motion is generated, whether the detected pulse waves are irregular by determining that an amplitude of the detected pulse waves is below a threshold value during a period of time, and whether the measured first blood pressure value varies during the measurement of the first biological information, wherein the measurement is suspended and resumed after a lapse of a prescribed period to start a calibration and a suspension of the measurement and the calibration are repeated after a lapse of a prescribed period until the calibration is completed in a case where it is not determined that the result of the measurement is normal based on at least one of the body motion being generated, the detected pulse waves being irregular, or the measured first blood pressure value varying, and the measurement is continued in other cases where it is determined that the result of the measurement is normal based on the body motion not being generated, the detected pulse waves not being irregular and the measured first blood pressure value failing to vary, and wherein the second biological information indicates a second blood pressure value.

10. A biological information measuring method in a biological information measuring apparatus including a sensing apparatus and a calibrating apparatus, the biological information measuring method comprising:

in the calibrating apparatus:

measuring a first blood pressure value as first biological information intermittently; and transmitting data containing the first biological information to the sensing apparatus, and in the sensing apparatus:

detecting pulse waves continuously in terms of time;

receiving the first biological information;

calibrating the pulse waves by the first biological information;

calculating second biological information from the calibrated pulse waves; and determining whether a result of measurement of the first biological information is normal based on whether body motion is generated, whether the detected pulse waves are irregular by determining that an amplitude of the detected pulse waves is below a threshold value during a period of time, and whether the measured first blood pressure value varies during the measurement of the first biological information, wherein the measurement is suspended and resumed after a lapse of a prescribed period to start a calibration and a suspension of the measurement and the calibration are repeated after a lapse of a predetermined period until the calibration is completed in a case where it is not determined that the result of the measurement is normal based on at least one of the body motion being generated, the detected pulse waves being irregular, or the measured first blood pressure value varying, and the measurement is continued in other cases where it is determined that the result of the measurement is normal based on the body motion not being generated, the detected pulse waves not being irregular, and the measured first blood pressure value failing to vary, and wherein the second biological information indicates a second blood pressure value.

11. A non-transitory computer readable medium storing a computer program which is executed by a computer to provide a method comprising the steps of:

measuring a first blood pressure value as first biological information intermittently;

transmitting data containing the first biological information;

detecting pulse waves continuously in terms of time;

receiving the first biological information;

calibrating the pulse waves by the first biological information;

calculating second biological information from the calculated pulse waves; and determining whether a result of measurement of the first biological information is normal based on whether body motion is generated, whether the detected pulse waves are irregular by determining that an amplitude of the detected pulse waves is below a threshold value during a period of time, and whether the measured first blood pressure value varies during the measurement of the first biological information, wherein the measurement is suspended and resumed after a lapse of a prescribed period to start a calibration and a suspension of the measurement and the calibration are repeated after a lapse of a predetermined period until the calibration is completed in a case where it is not determined that the result of the measurement is normal based on at least one of the body motion being generated, the detected pulse waves being irregular, or the measured first blood pressure value varying, and the measurement is continued in other cases where it is determined that the result of the measurement is normal based on the body motion not being generated, the detected pulse waves not being irregular and the measured first blood pressure value failing to vary, and wherein the second biological information indicates a second blood pressure value.

* * * * *